US008840647B2

(12) United States Patent
Siemionow et al.

(10) Patent No.: US 8,840,647 B2
(45) Date of Patent: Sep. 23, 2014

(54) FACET AUGMENTATION

(75) Inventors: Krzysztof B. Siemionow, Shaker Heights, OH (US); Isador H. Lieberman, Fort Lauderdale, FL (US)

(73) Assignee: The Cleveland Clinic Foundation, Cleveland, OH (US)

( * ) Notice: Subject to any disclaimer, the term of this patent is extended or adjusted under 35 U.S.C. 154(b) by 447 days.

(21) Appl. No.: 12/535,413

(22) Filed: Aug. 4, 2009

(65) Prior Publication Data

US 2010/0036418 A1 Feb. 11, 2010

Related U.S. Application Data

(60) Provisional application No. 61/086,252, filed on Aug. 5, 2008.

(51) Int. Cl.
*A61B 17/70* (2006.01)
*A61B 17/88* (2006.01)
*A61F 2/44* (2006.01)
*A61F 2/30* (2006.01)

(52) U.S. Cl.
CPC ..... *A61F 2/4405* (2013.01); *A61F 2002/30578* (2013.01); *A61F 2/442* (2013.01); *A61F 2310/00017* (2013.01); *A61F 2002/30563* (2013.01); *A61F 2002/449* (2013.01); *A61F 2002/3092* (2013.01); *A61B 17/7059* (2013.01)
USPC .......................................... 606/247; 606/279

(58) Field of Classification Search
USPC ......... 606/246–249, 257, 276–277, 279–283, 606/70–71, 298
See application file for complete search history.

(56) References Cited

U.S. PATENT DOCUMENTS

| 4,611,582 | A | | 9/1986 | Duff | |
|---|---|---|---|---|---|
| 5,180,393 | A | * | 1/1993 | Commarmond | 623/13.14 |
| 5,375,823 | A | | 12/1994 | Navas | |
| 5,387,213 | A | * | 2/1995 | Breard et al. | 606/254 |
| 5,607,425 | A | * | 3/1997 | Rogozinski | 606/264 |
| 5,707,372 | A | * | 1/1998 | Errico et al. | 606/252 |
| 6,645,208 | B2 | * | 11/2003 | Apfelbaum et al. | 606/71 |
| 6,835,205 | B2 | | 12/2004 | Atkinson et al. | |
| 7,101,398 | B2 | * | 9/2006 | Dooris et al. | 623/13.11 |
| 7,238,204 | B2 | * | 7/2007 | Le Couedic et al. | 623/17.11 |
| 7,846,183 | B2 | * | 12/2010 | Blain | 606/247 |
| 7,857,837 | B2 | * | 12/2010 | Lieponis | 606/280 |
| 8,075,596 | B2 | * | 12/2011 | Molz | 606/257 |
| 8,109,978 | B2 | * | 2/2012 | Ferree | 606/279 |
| 8,372,150 | B2 | * | 2/2013 | Humphreys et al. | 623/17.15 |
| 8,425,571 | B2 | * | 4/2013 | Bae et al. | 606/279 |
| 2003/0004572 | A1 | * | 1/2003 | Goble et al. | 623/17.11 |
| 2003/0135277 | A1 | * | 7/2003 | Bryan et al. | 623/17.12 |

(Continued)

FOREIGN PATENT DOCUMENTS

EP 1 221 308 A1 7/2002

*Primary Examiner* — Ellen C Hammond
*Assistant Examiner* — Jacqueline Johanas
(74) *Attorney, Agent, or Firm* — Tarolli, Sundheim, Covell & Tummino LLP (57) ABSTRACT

A method for augmenting or replacing a spinal facet (24) includes the steps of providing a first plate (40) and a second plate (50). An elastomeric member (70) is secured between and to the first plate (40) and the second plate (50). The first plate (40) is secured to a first vertebra (20). The second plate (50) is secured to a second vertebra (30) adjacent the first vertebra (20) for mimicking natural articulation between the first and second vertebrae (20, 30).

17 Claims, 7 Drawing Sheets

(56) References Cited

U.S. PATENT DOCUMENTS

| | | | |
|---|---|---|---|
| 2003/0191532 A1* | 10/2003 | Goble et al. | 623/17.11 |
| 2003/0220643 A1 | 11/2003 | Ferree | |
| 2004/0073215 A1 | 4/2004 | Carli | |
| 2004/0106995 A1* | 6/2004 | Le Couedic et al. | 623/17.11 |
| 2005/0131542 A1* | 6/2005 | Benzel et al. | 623/17.13 |
| 2005/0137706 A1* | 6/2005 | Reiley | 623/17.11 |
| 2005/0228381 A1* | 10/2005 | Kirschman | 606/61 |
| 2005/0240266 A1* | 10/2005 | Kuiper et al. | 623/17.11 |
| 2005/0245930 A1 | 11/2005 | Timm et al. | |
| 2005/0261682 A1* | 11/2005 | Ferree | 606/61 |
| 2005/0261774 A1* | 11/2005 | Trieu | 623/17.16 |
| 2006/0129239 A1* | 6/2006 | Kwak | 623/17.13 |
| 2006/0247633 A1* | 11/2006 | Winslow et al. | 606/61 |
| 2006/0247779 A1* | 11/2006 | Gordon et al. | 623/17.15 |
| 2006/0259142 A1* | 11/2006 | Dooris et al. | 623/13.15 |
| 2006/0271046 A1* | 11/2006 | Kwak et al. | 606/61 |
| 2006/0276794 A1* | 12/2006 | Stern | 606/69 |
| 2006/0282080 A1* | 12/2006 | Albert et al. | 606/61 |
| 2006/0293662 A1* | 12/2006 | Boyer et al. | 606/61 |
| 2007/0083200 A1* | 4/2007 | Gittings et al. | 606/61 |
| 2007/0123863 A1* | 5/2007 | Winslow et al. | 606/61 |
| 2007/0168035 A1* | 7/2007 | Koske | 623/17.13 |
| 2007/0185489 A1* | 8/2007 | Abdou | 606/61 |
| 2007/0198091 A1* | 8/2007 | Boyer et al. | 623/17.13 |
| 2007/0233076 A1* | 10/2007 | Trieu | 606/61 |
| 2007/0270972 A1* | 11/2007 | Gordon et al. | 623/17.16 |
| 2007/0282445 A1* | 12/2007 | Reiley | 623/17.11 |
| 2007/0299442 A1* | 12/2007 | Eisermann et al. | 606/61 |
| 2007/0299448 A1* | 12/2007 | Chin et al. | 606/69 |
| 2008/0027547 A1* | 1/2008 | Yu et al. | 623/17.13 |
| 2008/0039847 A1* | 2/2008 | Piper et al. | 606/69 |
| 2008/0097440 A1* | 4/2008 | Reiley et al. | 606/61 |
| 2008/0161854 A1* | 7/2008 | Bae et al. | 606/246 |
| 2008/0161928 A1* | 7/2008 | Trieu | 623/17.16 |
| 2008/0183209 A1 | 7/2008 | Robinson et al. | |
| 2008/0208260 A1* | 8/2008 | Truckai et al. | 606/280 |
| 2008/0234764 A1* | 9/2008 | Landry et al. | 606/86 A |
| 2009/0030462 A1* | 1/2009 | Buttermann | 606/249 |
| 2009/0326589 A1* | 12/2009 | Lemoine et al. | 606/280 |
| 2010/0004687 A1* | 1/2010 | Falahee | 606/246 |
| 2010/0234951 A1* | 9/2010 | Koske | 623/17.11 |
| 2011/0093012 A1* | 4/2011 | Gittings | 606/247 |

* cited by examiner

FACET AUGMENTATION

RELATED APPLICATION

This application claims the benefit of U.S. Provisional Patent Application No. 61/086,252, filed Aug. 5, 2008, the entirety of which is incorporated herein by reference.

TECHNICAL FIELD

The present invention relates to spinal stabilization instrumentation and, in particular, relates to a method and apparatus for augmenting or replacing the facet joints.

BACKGROUND OF THE INVENTION

The spinal column consists of a series of vertebrae that cooperate to provide articulation along the entire column. The column is divided up into lumbar, thoracic, and cervical vertebrae. Each pair of adjacent vertebrae includes a superior articular facet and an inferior articular facet that articulate to allow spinal motion during body movement. These facets are configured differently along the length of the spine to allow for varying degrees of articulation along several degrees of freedom.

There are numerous spinal disorders that may affect the vertebral articulation at the facet. The source of these disorders may be genetic, disease, trauma or the like. When one or both of the facets at a particular articulation site become damaged, surgical intervention may become desirable. Patients that suffer from such conditions usually experience extreme and debilitating pain, as well as altered nerve function or irritation. These spinal disorders, pathologies, and injuries limit the spine's range of motion and/or threaten the critical elements of the nervous system housed within the spinal column.

A variety of procedures and devices have been developed to repair damaged facets. These procedures, however, frequently involve resection of a portion, or the entire, damaged facet to provide suitable space for stabilizing instruments to be secured to the spine. These procedures can be invasive and can result in lengthy recovery time for the patient. Therefore, there is a need in the art for a device which helps restore spinal articulation in a minimally invasive manner.

SUMMARY OF THE INVENTION

In accordance with the present invention, a method for augmenting a spinal facet includes providing a first plate and a second plate. An elastomeric member is secured between and to the first plate and the second plate. The first plate is secured to a first vertebra. The second plate is secured to a second vertebra adjacent the first vertebra for mimicking natural articulation between the first and second vertebrae.

In accordance with another embodiment of the present invention, a method for replacing a spinal facet includes removing a facet joint between a first vertebra and an adjacent second vertebra. A first plate and a second plate are provided and an elastomeric member is secured between and to the first plate and the second plate. The first plate is secured to the first vertebra and the second plate is secured to the second vertebra for mimicking natural articulation between the first and second vertebrae.

In accordance with another embodiment of the present invention, an apparatus for augmenting a spinal facet is provided. The apparatus comprises first and second plates. Each of the first and second plates has an opening for receiving a fastener to fix the first and second plates to adjacent vertebrae. An elastomeric member is disposed between the first and second plates. The elastomeric member is fixed to both the first plate and the second plate to provide relative movement between the first and second plates to mimic the natural articulation between the adjacent vertebrae.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION

Figure 1:
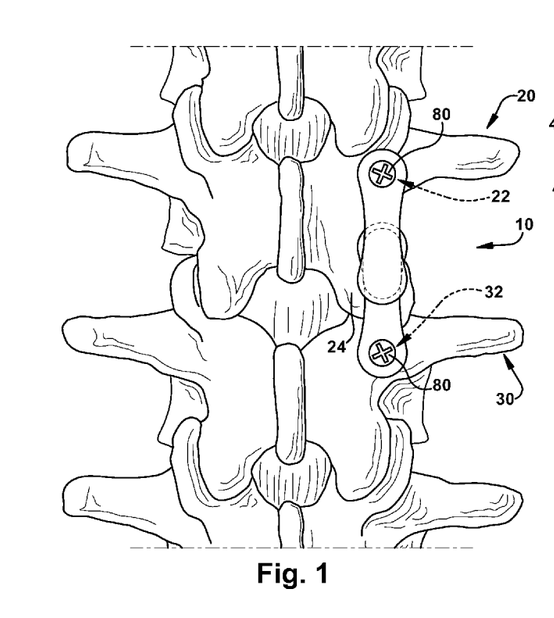
FIG. 1 is a schematic illustration of a facet augmentation device secured to a spine in accordance with an embodiment of the present invention.
Figure 2:
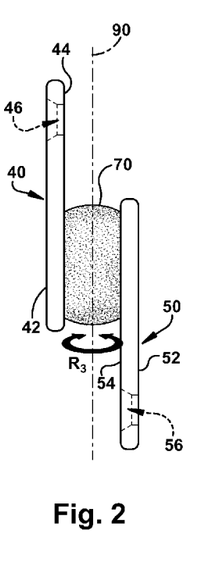
FIG. 2 is a side view of the device of FIG. 1.
Figure 3:
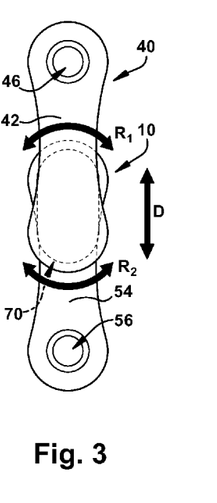
FIG. 3 is a front view of the device of FIG. 1.

The present invention relates to an apparatus and method for augmenting a spinal facet. FIGS. 1-3 illustrates a device 10 for augmenting a diseased or otherwise damaged facet 24 between adjacent first and second vertebrae 20, 30 of a spine. Although the lumbar vertebrae are illustrated, it will be understood that the device 10 may be used to repair a facet between any two adjacent vertebrae along the spine—including cervical and thoracic. Regardless of the particular spinal column placement, when implanted, the device 10 is secured to the pedicle 22 of the first vertebra 20 and the pedicle 32 of the second vertebra 30 such that the device extends parallel to and/or over the damaged facet 24 and generally along the spine.

As shown in FIGS. 2-3, the device 10 includes a first plate 40 and a second plate 50. The first plate 40 is substantially rectangular and includes a first surface 42 and a substantially parallel second surface 44. Alternatively, the first plate 40 can be oval, a combination of oval and rectangular, or otherwise suitably shaped given particular anatomical conditions. The first plate 40 further includes an opening 46 that extends from the first surface 42 to the second surface 44. The opening 46 is configured to receive a fastener for securing the first plate 40 to the first vertebra 20. The first plate 40 is rigid and may be formed from any suitable biocompatible material, such as metals, polymers or combinations thereof. For example, the first plate 40 could be made of a titanium alloy.

The second plate 50 is substantially rectangular and includes a first surface 52 and a substantially parallel second surface 54. Alternatively, the second plate 50 can be oval, a combination of oval and rectangular, or otherwise suitably shaped given particular anatomical conditions. The second plate 50 further includes an opening 56 that extends from the first surface 52 to the second surface 54. The opening 56 is configured to receive a fastener for securing the second plate 50 to the second vertebra 30. The second plate 50 is rigid and may be formed from any suitable biocompatible material, such as metals, polymers or combinations thereof. For example, the second plate 50 could be made of a titanium alloy.

The first plate 40 and the second plate 50 may be configured or otherwise adapted to promote bone ingrowth. In particular, the first surface 42 of the first plate 40 and the first surface 52 of the second plate 50 may be constructed of a porous material. Alternatively or additionally, the first surface 42 of the first plate 40 and the first surface 52 of the second plate 50 may be physically or chemically altered, coated or treated to promote bone ingrowth thereon.

The device 10 further includes an elastomeric member 70 positioned between the first plate 40 and the second plate 50. In particular, the elastomeric member 70 is fixed to the second surface 44 of the first plate 40 and the second surface 54 of the second plate 50. The elastomeric member 70 may be adhered or bonded to the first plate 40 and the second plate 50 in any manner known in the art. It is contemplated that the elastomeric member 70 could be insert molded, transfer molded or injection molded between the first plate 40 and the second plate 50. Alternatively, the first plate 40, the second plate 50, and the elastomeric member 70 may be molded or otherwise formed as a single piece.

The elastomeric member 70 has a one-piece construction and may be made of a urethane silicone blend manufactured by the Polymer Technology Group located in Berkley, Calif. or any other suitable source. Alternatively, the elastomeric member 70 may be made of a polymer that is a silicone-polycarbonate-urethane copolymer such as CarboSi® (manufactured by the Polymer Technology Group located in Berkley, Calif.). The elastomeric member 70 is prepared through a multi-step bulk synthesis during which polydimethylsiloxane is incorporated into the polymer soft segment with aliphatic, hydroxyl-terminated polycarbonate oligomers. The hard segment consists of an aromatic diisocyanate with a low molecular weight glycol chain extender. The copolymer chains are terminated with silicone.

The material of the elastomeric member 70 may combine the biocompatibility and biostability of silicone elastomers with the processibility and toughness of thermoplastic urethane elastomers. The material of the elastomeric member 70 has a relatively high hard segment content that softens to a strategically defined durometer/compliance upon reaching equilibrium with the body of a patient. The relevant equilibrium involves thermal equilibrium with the body at approximately 37° C. and equilibrium water and solute uptake by the polymer after being implanted in the body. The material of the elastomeric member 70 has a decreased modulus at 37° C. compared to that at room temperature. Accordingly, the higher durometer polymer can be used for its biostability, since conditions in the human body lower the modulus of the polymer to the desired range of compressive stiffness. Thus, the material of the elastomeric member 70 can be tailored such that the stiffness of the elastomeric member is adapted to suit a particular clinical objective and/or anatomical placement.

As shown in FIG. 2, the elastomeric member 70 is positioned between the first and second plates 40, 50 such that the opening 46 in the first plate and the opening 56 in the second plate are positioned on opposite sides of the elastomeric member. In this configuration, the opening 46 in the first plate 40, the opening 56 in the second plate 50, and the elastomeric member 70 may be substantially aligned with one another in the longitudinal direction (see FIG. 3). Alternatively, the first plate 40 and the second plate 50 could be offset from one another relative to the elastomeric member 70 in one or more directions (not shown).

The device 10 is assembled such that the first plate 40 and the second plate 50 each extend approximately to a respective end of the elastomeric member 70. In other words, the first plate 40 and the second plate 50 overlap one another in the longitudinal direction. The first plate 40 and/or the second plate 50 could, however, be secured to the elastomeric member 70 such that the opening 46 in the first plate and the opening 56 in the second plate are further or closer together.

The material properties of the elastomeric member 70 allow the first plate 40 to articulate relative to the second plate 50 when the elastomeric member is fixed to the first plate and the second plate. Due to the configuration and anatomical placement of the device 10, the articulation of the device may be designed to mimic the natural articulation between the superior articular facet and the inferior articular facet on adjacent vertebrae (not shown). More specifically, the construction of the device 10 may allow the elastomeric member 70 to deflect under tension, compression or shear without plastic deformation.

The articulation between the first and second plates 40, 50 may occur in one or more degrees of freedom in order to adequately mimic natural spinal articulation. For example, the first plate 40 may rotate in a direction indicated by arrow R1 relative to the second plate 50 and the second plate may rotate in a direction indicated by arrow R2 relative to the first plate (FIG. 3). These rotations mimic the natural rotation between the superior and inferior articular facets during lateral flexion of the spine. Additionally, the first plate 40 and the second plate 50 may move longitudinally relative to one another along the direction indicated by arrow D to mimic the natural movement between the superior articular facet and the inferior articular facet during flexion and extension of the spine.

Furthermore, the first plate 40 and the second plate 50 may tilt about an axis 90 relative to one another in a direction indicated by arrow R3 (FIG. 2) to mimic the natural rotation of the superior and inferior articular facets during rotation of the spine during, for example, rotation of the shoulders about the hips (not shown). Although several degrees of freedom are illustrated, those skilled in the art will appreciate that the device 10 may be configured to provide more or fewer degrees of freedom for each plate 40 and 50.

The device 10 is positioned near or over the damaged facet 24 such that the device undergoes the same or similar articulating forces naturally exhibited at the facet, such as those previously discussed. The device 10 may be positioned such that the first plate 40 and the second plate 50 are fastened to the spine in the coronal plane or the sagittal plane or anything in between depending on anatomical considerations and treatment objectives. The plates 40, 50 may be secured between and to any spinal structure along or around the aforementioned planes. This may include, but is not limited to, the pedicles, transverse processes, spinous processes, facets, and combinations thereof. Although FIGS. 1-4 illustrate the device 10 implanted on only the right lateral side of the spine, those having ordinary skill will appreciate that the device could alternatively or additionally be implanted on the left lateral side of the spine.

As shown in FIG. 1, to install the device 10, the opening 46 of the first plate 40 is aligned with the pedicle 22 of the first vertebra 20 and the opening 56 of the second plate 50 is aligned with the pedicle 32 of the second vertebra 30. In particular, the first plate 40 is secured to the vertebra 20 superior to the vertebra 30 to which the second plate 50 is secured. A fastener 80 is then fed through the opening 46 in the first plate 40 to secure the first plate to the pedicle 22 of the first vertebra 20. Likewise, a fastener 80 is fed through the opening 56 in the second plate 50 to secure the second plate to the pedicle 32 of the second vertebra 30.

Figure 4:
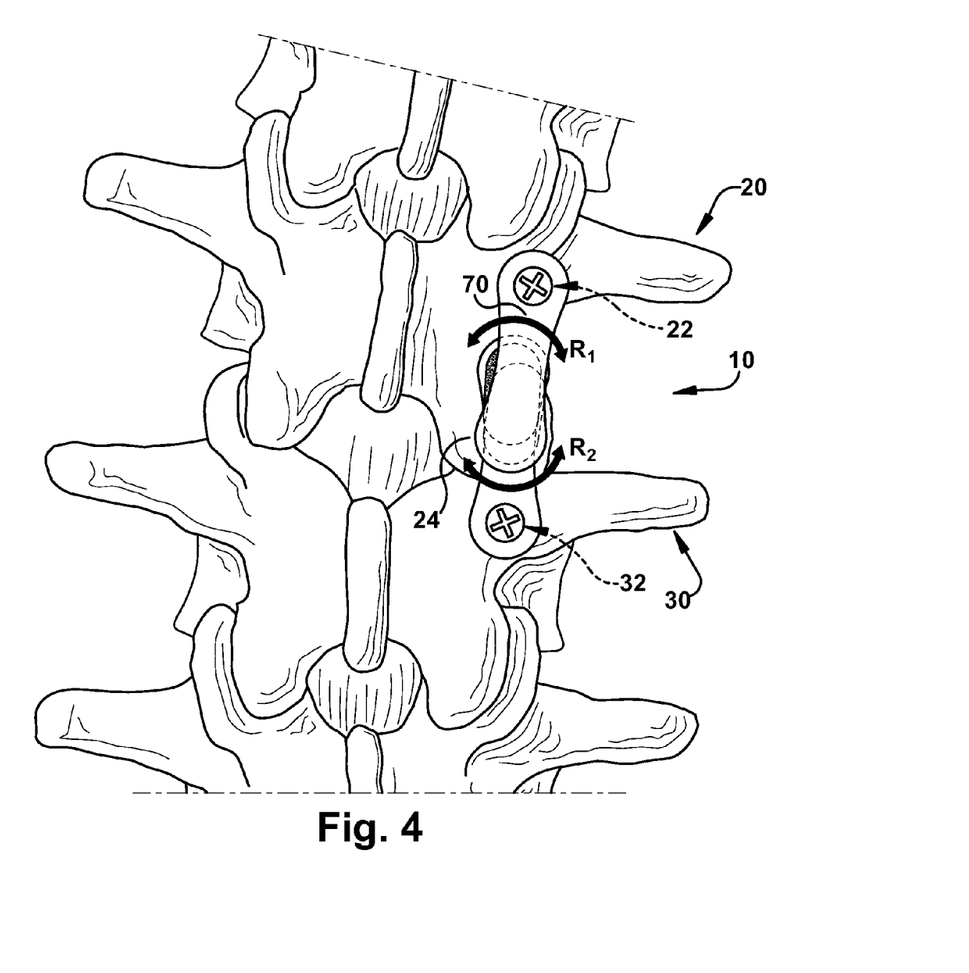
FIG. 4 is a schematic illustration of the device of FIG. 1 during spinal articulation.

By securing the plates 40, 50 directly to the vertebrae 20, 30, when body movement causes spinal articulation, the plates likewise experience movement. One example of such articulated movement is illustrated in FIG. 4 in which the spine is laterally flexed. When the vertebrae 20, 30 move relative to each other during lateral flexion, the first plate 40 moves with the pedicle 22 on the first vertebra, and the second plate 50 likewise moves with the pedicle 32 on the second vertebra. The articulation between the first plate 40 and the second plate 50 is experienced at, and borne by, the elastomeric member 70 in at least the directions R1 and R2. Accordingly, the first and second plates 40, 50 rely on the elastomeric member 70 in order to mimic the natural articulation between the adjacent vertebrae 20, 30.

The device 10 may include additional or alternative structure designed to provide additional stability to the device to help ensure functionality and reliability. For example, the fasteners 80 may be configured to resist longitudinal and/or rotational displacement relative to the first plate 40 and the second plate 50 in order to prevent the fasteners from loosening or otherwise backing out of the pedicles 22, 32 during movement of the vertebrae 20, 30. The heads of the fasteners 80 may therefore include structure such as ratchet teeth, deflectable tines, knurls or the like that mate with or otherwise engage complementary structure adjacent the openings 46, 56 of the first and second plates 40, 50, respectively, to prevent movement of the fasteners relative to the first and second plates. By preventing such relative movement, the first plate 40 and the second plate 50 are held rigidly against the bone to ensure that the articulation between the first plate and the second plate is properly borne by the elastomeric member 70 and, thus, the device 10 adequately mimics the natural articulation between the adjacent vertebrae 20, 30.

When the spine naturally articulates during body movement, the forces normally borne by the damaged facet 24 are shared or transferred to the device 10 and, particularly, to the elastomeric member 70. The device 10 thereby modulates facet function by acting as a dampener to unrestricted pathologic motion. Therefore the device 10 of the present invention can structurally augment the damaged facet 24 without requiring partial or full resection of the damaged facet, thereby advantageously sparing spinal tissue.

Figure 5:
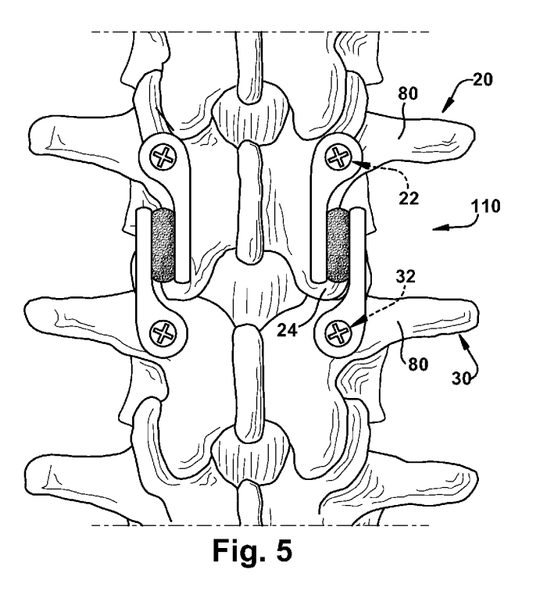
FIG. 5 is a schematic illustration of a facet augmentation device secured to a spine in accordance with an alternative embodiment of the present invention.
Figure 6:
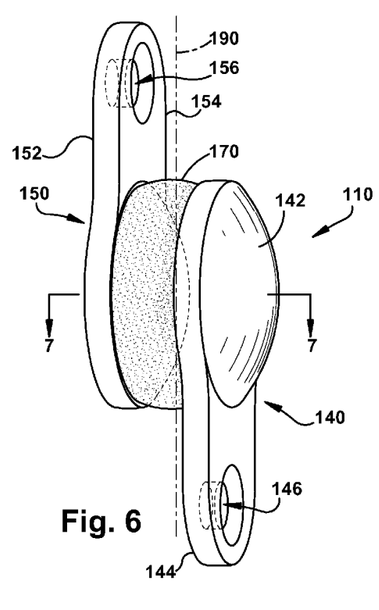
FIG. 6 is a side view of the device of FIG. 5.
Figure 7:
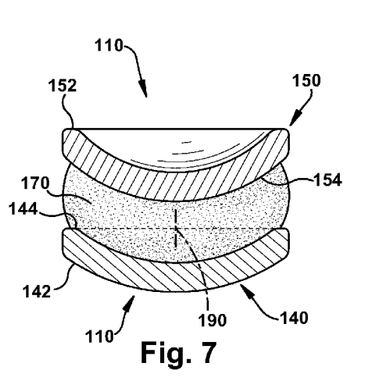
FIG. 7 is a sectional view taken along line 7-7 of FIG. 6 of the device.

In accordance with another aspect of the present invention, the device may include elements which are curved or shaped to match bone contours of the spine depending on anatomical considerations and treatment objectives. As shown in FIGS. 5-7, the device 110 extends generally along a central axis 190 and includes a first plate 140 and a second plate 150. The first and second plates 140, 150 are similar in construction to the first and second plates 40, 50 illustrated in FIGS. 1-4 except that the first and second plates in FIGS. 5-7 are shaped to match bone contours of the spine. The device 110 may be used to augment a diseased or otherwise damaged facet 24 on either or both sides of the median plane between the first and second vertebrae 20, 30 of the spine (FIG. 5).

The first plate 140 includes a first surface 142 and a substantially parallel second surface 144. The first surface 142 and the second surface 144 may exhibit a concave profile relative to the central axis 190 of the device 110. The first plate 140 further includes an opening 146 that extends from the first surface 142 to the second surface 144. The opening 146 is configured to receive a fastener for securing the first plate 140 to the first vertebra 120. The first plate 140 is rigid and may be formed from any suitable biocompatible material, such as metals, polymers or combinations thereof. For example, the first plate 140 could be made of a titanium alloy.

The second plate 150 includes a first surface 152 and a substantially parallel second surface 154. The first surface 152 and the second surface 154 may exhibit a convex profile relative to the central axis 190 of the device 110. The second plate 150 further includes an opening 156 that extends from the first surface 152 to the second surface 154. The opening 156 is configured to receive a fastener for securing the second plate 150 to the second vertebra 130. The second plate 150 is rigid and may be formed from any suitable biocompatible material, such as a metals, polymers or combinations thereof. For example, the second plate 150 could be made of a titanium alloy.

The first plate 140 and the second plate 150 may be configured or otherwise adapted to promote bone ingrowth. In particular, the first surface 142 of the first plate 140 and the first surface 152 of the second plate 150 may be constructed of a porous material. Alternatively or additionally, the first surface 142 of the first plate 140 and the first surface 152 of the second plate 150 may be physically or chemically altered, coated or treated to promote bone ingrowth thereon.

The device 110 further includes an elastomeric member 170 positioned between the first plate 140 and the second plate 150. In particular, the elastomeric member 170 is fixed to the second surface 144 of the first plate 140 and the second surface 154 of the second plate 150. The elastomeric member 170 may be constructed of a material similar to the construction of the elastomeric member 70. The elastomeric member 170 may be adhered or bonded to the first plate 140 and the second plate 150 in any manner known in the art. It is contemplated that the elastomeric member 170 could be insert molded, transfer molded or injection molded between the first plate 140 and the second plate 150. Alternatively, the first plate 140, the second plate 150, and the elastomeric member 170 may be molded or otherwise formed as a single piece. Regardless of the method of constructing the device 110, when the device is assembled, the concave surfaces 142, 144 of the first plate 140 extend substantially parallel to the concave surfaces 152, 154 of the second plate 150.

Similar to the device 10 illustrated in FIGS. 1-4, when the elastomeric member 170 is fixed to the first plate 140 and the second plate 150, the material properties of the elastomeric member allow the first plate to articulate relative to the second plate in a manner designed to mimic the natural articulation between the superior articular facet and the inferior articular facet on adjacent vertebrae (not shown). More specifically, the construction of the device 110 may allows the elastomeric member 70 to deflect under tension, compression, or shear without plastic deformation. Furthermore, the congruent relation between the concave second surface 144 of the first plate 140 and the convex second surface 154 of the second plate 150 reduces the shear forces borne by the elastomeric member 170 as the first plate and the second plate articulate relative to one another thereby increasing the durability and reliability of the device 110.

Figure 8:
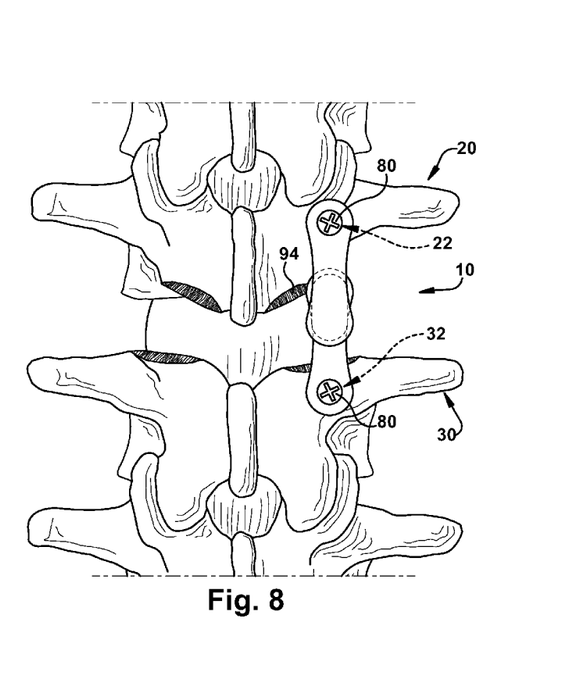
FIG. 8 is a schematic illustration of a facet augmentation device secured to a spine in accordance with another embodiment of the present invention.

In accordance with another aspect of the present invention, the device may be used to replace a damaged facet that has been surgically removed. The patient's anatomy, the degree of facet deterioration, and other clinical factors may make it desirous to fully replace—rather than augment—the facet. As shown in FIG. 8, when one or both facets 94 between the first and second vertebrae 20, 30 become diseased or otherwise damaged such that vertebral articulation is compromised, those facets may be surgically resected. Although the device 10 is illustrated, it will be understood that the device 110 or alternative configurations thereof may likewise be used. When the device 10 is subsequently secured to the first vertebra 20 and the second vertebra 30, the device fully replaces the facet 94 and, thus, completely bears the articulation forces normally borne by the facet.

Figure 9:
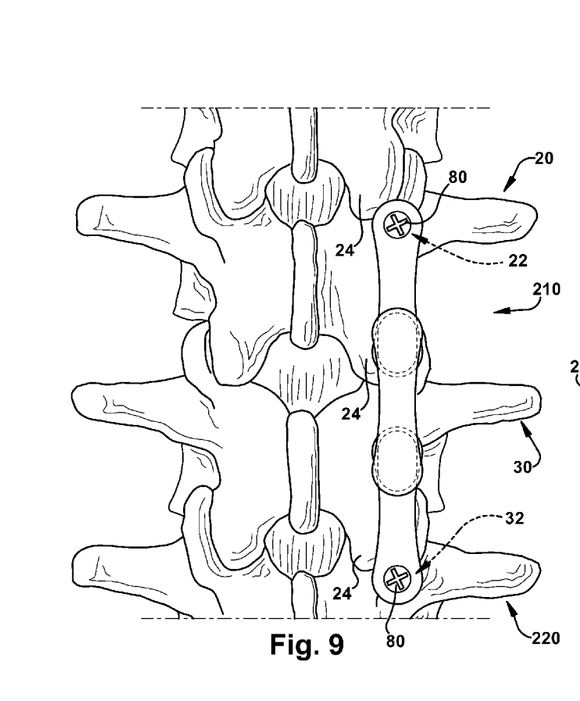
FIG. 9 is a schematic illustration of a facet augmentation device secured to a spine in accordance with another embodiment of the present invention.
Figures 10, 11:
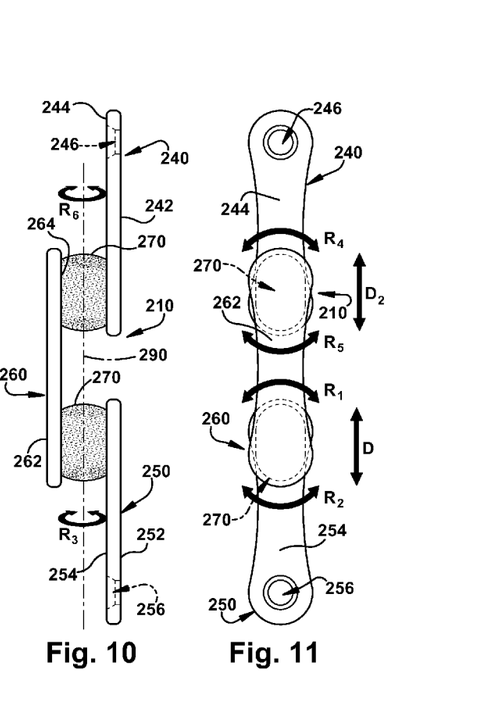
FIG. 10 is a side view of the device of FIG. 9.
FIG. 11 is a front view of the device of FIG. 9.

In accordance with another aspect of the present invention, the device may be configured to augment multiple facets along the same lateral side of the spine. As shown in FIGS. 9-11, the device 210 extends generally along a central axis 290 and includes a first plate 240, a second plate 250, and a third plate 260. The first, second, and third plates 240, 250, 260 are similar in construction to the first and second plates 40, 50 illustrated in FIGS. 1-4. The device 210 may be used to augment more than one diseased or otherwise damaged facet 24 between adjacent first, second, and third vertebrae 20, 30, 220 of the spine (FIG. 9).

The first plate 240 includes a first surface 242 and a substantially parallel second surface 244. The first plate 240 further includes an opening 246 that extends from the first surface 242 to the second surface 244. The opening 246 is configured to receive a fastener 80 for securing the first plate 240 to the first vertebra 220. The first plate 240 is rigid and may be formed from any suitable biocompatible material, such as metals, polymers or combinations thereof. For example, the first plate 240 could be made of a titanium alloy.

The second plate 250 includes a first surface 252 and a substantially parallel second surface 254. The second plate 250 further includes an opening 256 that extends from the first surface 252 to the second surface 254. The opening 256 is configured to receive a fastener 80 for securing the second plate 250 to the third vertebra 220. The second plate 250 is rigid and may be formed from any suitable biocompatible material, such as a metals, polymers or combinations thereof. For example, the second plate 250 could be made of a titanium alloy.

The first plate 240 and the second plate 250 may be configured or otherwise adapted to promote bone ingrowth. In particular, the first surface 242 of the first plate 240 and the first surface 252 of the second plate 250 may be constructed of a porous material. Alternatively or additionally, the first surface 242 of the first plate 240 and the first surface 252 of the second plate 250 may be physically or chemically altered, coated or treated to promote bone ingrowth thereon. Moreover, the first plate 240 and the second plate 250 may be contoured to portions of the first vertebra 20 and the third vertebra 220.

The third plate 260 includes a first surface 262 and a substantially parallel second surface 264. The third plate 260 is rigid and may be formed from any suitable biocompatible material, such as a metals, polymers or combinations thereof. For example, the third plate 260 could be made of a titanium alloy.

The device 210 further includes a pair of elastomeric members 270. One elastomeric member 270 is positioned between the first plate 240 and the third plate 260 and the other elastomeric member is positioned between the second plate 250 and the third plate. In particular, one elastomeric member 270 is fixed to the second surface 244 of the first plate 240 and the second surface 264 of the third plate 260. The other elastomeric member 270 is fixed to the second surface 254 of the second plate 250 and the second surface 264 of the third plate 260. The elastomeric members 270 may be constructed of a material similar to the construction of the elastomeric member 70. The elastomeric members 270 may be adhered or bonded to the first plate 240, the second plate 250, and the third plate 260 in any manner known in the art. It is contemplated that the elastomeric members 270 could be insert molded, transfer molded or injection molded between the first plate 240 and the third plate 260 and between the second plate 250 and the third plate, respectively. Alternatively, the first plate 240, the second plate 250, the third plate 260, and both elastomeric members 270 may be molded or otherwise formed as a single piece.

Similar to the device 10 illustrated in FIGS. 1-4, when the elastomeric member 270 of the device 210 is fixed to the second plate 250 and the third plate 260, the material properties of the elastomeric member allows the second plate to articulate relative to the third plate in a manner designed to mimic the natural articulation between the superior articular facet on the second vertebra 30 and the inferior articular facet on the third vertebra 220. The articulation between the second and third plates 250, 260 may occur in one or more degrees of freedom in order to adequately mimic natural spinal articulation. For example, the third plate 260 may rotate in the direction R1 relative to the second plate 250 and the second plate may rotate in the direction R2 relative to the third plate (FIG. 11). These rotations mimic the natural rotation between the superior and inferior articular facets of the second vertebra 30 and the third vertebra 220 during lateral flexion of the spine. Additionally, the second plate 250 and the third plate 260 may move longitudinally relative to one another along the direction D to mimic the natural movement between the superior articular facet and the inferior articular facet of the second vertebra 30 and the third vertebra 220 during flexion and extension of the spine.

Furthermore, when the elastomeric member 270 is fixed to the first plate 240 and the third plate 260, the material properties of the elastomeric member allows the first plate to articulate relative to the third plate in a manner designed to mimic the natural articulation between the superior articular facet on the first vertebra 20 and the inferior articular facet on the second vertebra 30. For example, the first plate 240 may rotate in a direction indicated by arrow R4 relative to the third plate 260 and the third plate may rotate in a direction indicated by arrow R5 relative to the first plate (FIG. 11). These rotations mimic the natural rotation between the superior and inferior articular facets of the first vertebra 20 and the second vertebra 30 during lateral flexion of the spine. Additionally, the first plate 240 and the third plate 260 may move longitudinally relative to one another along the direction indicated by arrow D2 to mimic the natural movement between the superior articular facet and the inferior articular facet of the first vertebra 20 and the second vertebra 30 during flexion and extension of the spine.

Due to this configuration, the device 210 is capable of providing structural augmentation to two damaged facets 24 between three consecutive vertebrae 20, 30, 220. Since the elastomeric members 270 may each independently deflect under tension, compression, or shear without plastic deformation, the device 210 may mimic the natural articulation between two consecutive pairs of vertebrae.

Figure 12:
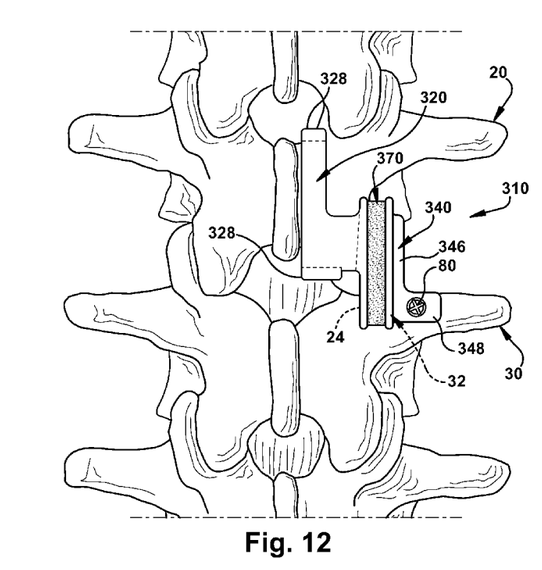
FIG. 12 is a schematic illustration of a facet augmentation device secured to a spine in accordance with another embodiment of the present invention.
Figure 13:
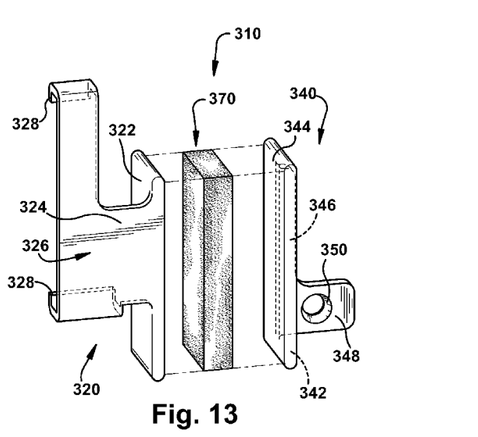
FIG. 13 is an exploded side view of the device of FIG. 12.

In another aspect of the present invention, the device may be secured to the vertebrae without the use of additional fasteners or hardware. As shown in FIGS. 12-13, the device 310 includes a first plate 320 secured to the first vertebra 20 without a fastener and a second plate 340 secured to the second vertebra 30 with a fastener 80.

The first plate 320 includes a substantially rectangular base 322 and a connecting portion 324 extending transversely from the base. A fastening portion 326 extends from the connecting portion 324 and includes fastening structure 328 for securing the first plate 320 to the first vertebra 20. The structure 328 may constitute one or more hooks, claws, projections or may otherwise have any configuration adapted to secure the first plate 320 to the first vertebra 20 without using separate fasteners. The first plate 320 is rigid and may be formed from any suitable biocompatible material, such as metals, polymers or combinations thereof.

As shown in FIG. 13, the fastening structure 328 constitutes a pair of opposing, U-shaped hooks 328 that are sized and shaped to engage the first vertebra 20. In particular, the hooks 328 are constructed to flex away from one another in order to snap onto the first vertebra 20. The hooks 328 may also be physically or chemically treated to promote bone ingrowth. Although FIGS. 12-13 illustrate that only the first plate 320 includes fastening structure 328, the second plate 340 may additionally or alternatively include such structure.

The second plate 340 is substantially rectangular and includes a first surface 342 and a substantially parallel second surface 344. A flange 346 extends from the first surface 342 and includes a projection 348. The projection 348 includes an opening 350 configured to receive a fastener 80 for securing the second plate 340 to the second vertebra 30. The second plate 340 is rigid and may be formed from any suitable biocompatible material, such as metals, polymers or combinations thereof.

The device 310 further includes an elastomeric member 370 positioned between the first plate 320 and the second plate 340. In particular, the elastomeric member 370 is fixed to the base 322 of the first plate 320 and the second surface 344 of the second plate 340. The elastomeric member 370 may be adhered or bonded to the first plate 320 and the second plate 340 in any manner known in the art. It is contemplated that the elastomeric member 370 could be insert molded, transfer molded or injection molded between the first plate 320 and the second plate 340. Alternatively, the first plate 320, the second plate 340, and the elastomeric member 370 may be molded or otherwise formed as a single piece.

To install the device 310, a fastener 80 is fed through the opening 350 in the second plate 340 to secure the second plate to the pedicle 32 of the second vertebra 30. The hooks 328 on the first plate 320 are then snapped onto the first vertebra 30 to secure the first plate to the first vertebra. In particular, one hook 328 is snapped over the superior lamina of the first vertebra 20 and the other hook 328 is snapped under the inferior lamina of the first vertebra. As with the device 10, when the plates 320, 340 are secured to the vertebrae 20, 30, the elastomeric member 370 cooperates with the plates such that the device 310 mimics natural spinal articulation during movement of the spine. By eliminating the need for additional fasteners, the device 310 not only reduces the number of parts and time for installation but also reduces the number of connections in the device susceptible to loosening, corrosion, wear, etc.

Figure 14:
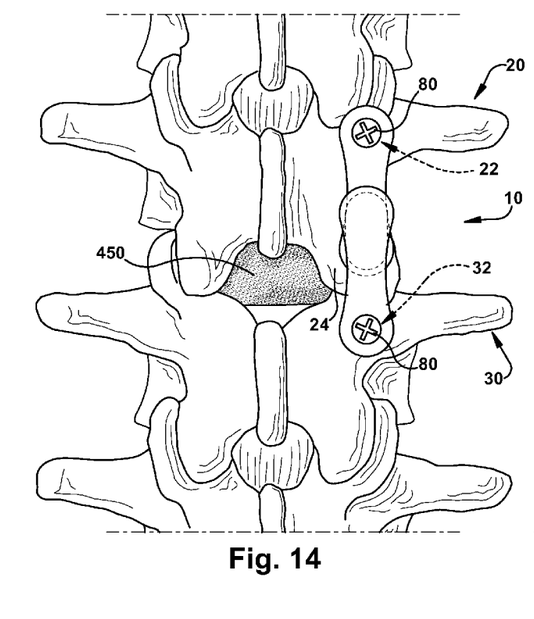
FIG. 14 is a schematic illustration of a facet augmentation device secured to a spine in accordance with another embodiment of the present invention.
Figure 15:
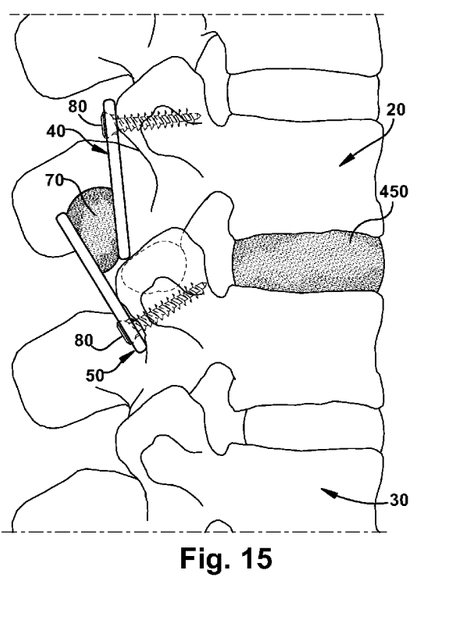
FIG. 15 is a side view of the device of FIG. 14 secured to the spine.

In another embodiment of the present invention, the device may be used in conjunction with an artificial disc replacement (ADR) prosthesis as shown in FIGS. 14-15. ADR is typically used to replace painful, arthritic or otherwise worn-out intervertebral disc of the lumbar spine with a metal or plastic prosthesis. Although ADR are beneficial to traditional spinal fusion procedures, the ADR prosthesis still affects the load distribution to the vertebrae adjacent the replacement site. Modified stress levels in vertebrae have been found to be attributable to adjacent segment disease. By placing the device of the present invention adjacent to the ADR prosthesis, the device may help reduce the degree to which the load distribution is affected and, thus, may help to prevent or delay adjacent segment disease.

As shown in FIGS. 14-15, once the ADR prosthesis 450 is implanted between adjacent vertebrae 20, 30 the device 10 may be secured superior to the prosthesis on adjacent vertebrae. Alternatively or additionally, the device 10 may be secured inferior to the ADR prosthesis 450 (not shown). Moreover, although the device 10 is illustrated as being secured on the right lateral side of the spine, the device could alternatively or additionally be secured on the left lateral side of the spine.

From the above description of the invention, those skilled in the art will perceive improvements, changes and modifications. Such improvements, changes and modifications within the skill of the art are intended to be covered by the appended claims. For example, features illustrated in a single embodiment may be incorporated into alternate or additional embodiments within the spirit of the present invention.

Having described the invention, the following is claimed:

1. A method for augmenting a spinal facet of a spinal column, the method comprising the steps of:
   providing a first plate and a second plate and an elastomeric member secured between and to the first plate and the second plate and extending along an axis that is parallel to a greatest dimension of the first plate and parallel to an axis of the spinal column extending in a cephalocaudal direction, the first and second plates being spaced entirely from the axis of the elastomeric member;
   placing a fastener through an opening in the first plate to secure the first plate to a first vertebra overlying the native facet of the first vertebra; and
   securing the second plate to a second vertebra overlying the native facet of the second vertebra such that an axis extending solely in an anterior-posterior direction intersects the first plate, the second plate, and the elastomeric member and such that no part of the first plate, the second plate, and the elastomeric member extends within the facet joint, the second vertebra being adjacent the first vertebra such that the first plate and the second plate mimic natural articulation between the first and second vertebrae.

2. The method of claim 1 wherein the step of securing the first plate to the first vertebra comprises securing the first plate to at least one of a pedicle, a transverse process, a spinous process, a lamina and the facet of the first vertebra and the step of securing the second plate to the second vertebra comprises securing the second plate to at least one of a pedicle, a transverse process, a spinous process, a lamina and the facet of the second vertebra.

3. The method of claim 1 further comprising the step of replacing the vertebral disc of the first vertebra with an artificial disc replacement prosthesis.

4. The method of claim 1, wherein the first plate and the second plate are adapted to mimic lateral flexion between the first and second vertebrae.

5. The method of claim 1, wherein the step of providing an elastomeric member comprises providing an elastomeric member formed from a urethane silicone blend or a silicone-polycarbonate-urethane copolymer.

6. The method of claim 1, wherein the first plate is shaped to match the contour of the first vertebra and the second plate is shaped to match the contour of the second vertebra.

7. The method of claim 6, wherein each of the first and second plates is one of concave or convex.

8. The method of claim 1, wherein the elastomeric member deflects under tension, compression, and shear without plastic deformation.

9. The method of claim 1 further comprising:
placing a fastener through an opening in the second plate to secure the second plate to the second vertebra, the openings in the first plate and the second plate being aligned with the elastomeric member in a longitudinal direction extending along the first and second plates.

10. The method of claim 1, wherein the second plate has a length that extends substantially parallel to the axis, the elastomeric member being positioned between the first plate and the second plate in a direction that extends substantially perpendicular to the axis and through the first plate and second plate.

11. The method of claim 1 comprising securing the first plate and the second plate to the elastomeric member such that the length of the first plate and a length of the second plate extend substantially parallel to one another.

12. The method of claim 1 comprising securing the first plate and the second plate to the elastomeric member such that the first plate and second plate overlap one another in the anterior-posterior direction.

13. The method of claim 1 comprising securing a surface of the first plate to the elastomeric member such that the surface faces towards the first vertebra when the first plate is secured to the first vertebra.

14. The method of claim 13 comprising securing a surface of the second plate to the elastomeric member such that the surface of the second plate faces away from the second vertebra when the second plate is secured to the second vertebra.

15. The method of claim 1, wherein the first plate and the second plate extend longitudinally in a linear direction.

16. The method of claim 1 comprising positioning the entire first plate posterior of the second plate.

17. A method for augmenting a spinal facet of a spinal column, the method comprising the steps of:
providing a first plate and a second plate and an elastomeric member secured between and to the first plate and the second plate and extending along an axis that is parallel to a greatest dimension of the first plate, parallel to a greatest dimension of the second plate, and parallel to an axis of the spinal column extending in a cephalocaudal direction, the first and second plates being spaced entirely from the axis of the elastomeric member;
securing the first plate directly to a first vertebra overlying the native facet of the first vertebra; and
securing the second plate to a second vertebra overlying the native facet of the second vertebra such that the first plate, the second plate, and the elastomeric member are aligned along an anterior-posterior direction extending away from the first and second vertebrae, the second vertebra being adjacent the first vertebra such that the first plate and the second plate mimic natural articulation between the first and second vertebrae.

* * * * *